(12) United States Patent
Moore (10) Patent No.: US 7,262,025 B2
(45) Date of Patent: Aug. 28, 2007

(54) HYBRID VECTOR HAVING A CYTOMEGALOVIRUS ENHANCER AND MYELOPROLIFERATIVE SARCOMA VIRUS PROMOTER

(75) Inventor: Margaret Dow Moore, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 94 days.

(21) Appl. No.: 10/465,156

(22) Filed: Jun. 18, 2003

(65) Prior Publication Data

US 2003/0232414 A1 Dec. 18, 2003

Related U.S. Application Data

(60) Provisional application No. 60/389,612, filed on Jun. 18, 2002.

(51) Int. Cl.
| | |
|---|---|
| C12N 5/10 | (2006.01) |
| C12N 15/85 | (2006.01) |
| C12N 15/63 | (2006.01) |
| C12N 15/64 | (2006.01) |
| C12P 21/00 | (2006.01) |
| C07K 14/745 | (2006.01) |

(52) U.S. Cl. .................. 435/69.1; 435/320.1; 435/325; 435/358; 435/455; 435/461

(58) Field of Classification Search ............. 435/320.1, 435/235.1, 325, 354, 352, 358, 366, 69.1; 536/23.1, 24.1
See application file for complete search history.

(56) References Cited

U.S. PATENT DOCUMENTS 6,166,178 A * 12/2000 Cech et al. ................. 530/324
7,038,032 B2 * 5/2006 Sheppard et al. .......... 536/23.5
2002/0002277 A1 * 1/2002 Maliszewski et al. ...... 536/23.5
2003/0054458 A1 * 3/2003 Baker et al. ................ 435/69.1
2003/0103986 A1 * 6/2003 Rixon et al. ............. 424/178.1

FOREIGN PATENT DOCUMENTS

WO WO00/65074 11/2000

OTHER PUBLICATIONS

Chinnasamy et al., "Lentiviral-medicated gene transfer into human lymphocytes: role of HIV-1 accessory proteins" *Blood* 96(4):1309-1316, Aug. 2000.

Plavec et al., "High transdominant RevM10 protein levels are required to inhibit HIV-1 replication in cell lines and primary T cells: implication for gene therapy of AIDS" *Gene Therapy* 4:128-139, 1997.

Stacey et al., "Comparison of *Myeloproliferative sarcoma* Virus with Moloney Murine Sarcoma Virus Variants by Nucleotide Sequencing and Heteroduplex Analysis" *Journal of Virology* 50(3):725-732, Jun. 1984.

Stocking et al., "Long terminal repeat sequences impart hematopoietic transformation properties to the *Myeloproliferative sarcoma* virus" *Proc. Natl. Acad. Sci. USA* 82:5746-5750, Sep. 1985.

Boshart et al., "A Very Strong Enhancer is Located Upstream of an Immediate Early Gene of Human Cytomegalovirus" *Cell* 41:521-530, Jun. 1985.

Chee, EMBL Database Accession No. X17403, Apr. 2005.
Stacy, EMBL Database Accession No. K01683, Apr. 2005.

* cited by examiner

*Primary Examiner*—David Guzo
(74) *Attorney, Agent, or Firm*—Michelle Lewis

(57) ABSTRACT

An expression vector capable of expressing high levels of heterologous proteins having a cytomegalovirus (CMV) enhancer 5' upstream from a myeloproliferative sarcoma virus (MPSV) promoter.

10 Claims, 2 Drawing Sheets

Figure 1

HYBRID VECTOR HAVING A CYTOMEGALOVIRUS ENHANCER AND MYELOPROLIFERATIVE SARCOMA VIRUS PROMOTER

CROSS-REFERENCE TO RELATED APPLICATION

This application claims the benefit under 35 U.S.C. 119(e) of provisional application No. 60/389,612, filed Jun. 18, 2002.

INTRODUCTION

The present invention is related to the construction and utilization of a DNA plasmid vector, in particular, those hybrid non-retroviral vectors that comprise the cytomegalovirus (CMV) enhancer and the myeloproliferative sarcoma virus (MPSV) promoter minus its negative control region. This hybrid sequence promotes the high expression of cloned genes under its transcriptional control when the vector is transfected into mammalian cell lines. Preferably, the vector also comprises other functional sequences to increase expression of the cloned sequence such as the Ig intron sequence, a viral internal ribosome entry site (IRES), a leader sequence to allow for secreted protein expression, and polyadenylation signals. The vector can also comprise selectable markers and other features that facilitate the replication of the vector in mammalian, yeast, and prokaryotic host cells, thus increasing the stability of the vector in whatever expression system is being used.

BACKGROUND OF THE INVENTION

The expression of foreign proteins by bacteria, yeast or mammalian cell lines has become routine. One type of commonly used means involves the construction of virion-plasmid hybrid vectors that possess the capacity to express cloned inserts in mammalian cells. The expression of the cloned gene with such hybrid vectors can occur in a transient, extrachromosomal manner, but higher production is usually obtained through random insertion of the vector into the host cell genome. The typical mammalian expression vector will contain regulatory elements, usually in the form of viral promoter or enhancer sequences and characterized by a broad host and tissue range, a polylinker sequence facilitating the insertion of a DNA fragment within the plasmid vector, and the sequences responsible for intron splicing and polyadenylation of mRNA transcripts. This contiguous region of promoter-polylinker-polyadenylation site is commonly referred to as the transcription unit. Viral promoter and enhancer regions have long been utilized as regulatory elements for use in mammalian host cells. For example, the strength of the CMV enhancer caused it to be a suggested component in eukaryotic expression vectors upon its discovery (Boshart et al., Cell, 41 (2):521-30 (1985)) and it has been utilized as a universal cell control element in transgenic mice (Schmidt et al. Mol. Cell. Biol. 10: 4406-4411 (1990)). The MPSV promoter coveys a wide host cell specificity to the virus including fibroblasts and hematopoietic stem cells (Stocking et al. Proc. Natl. Acad. Sci. USA, 82: 5746-5750 (1985)). Accordingly, this promoter has been used to express heterologous genes in a number of cell types, including skin fibroblasts (Pamer et al., Blood, 73: 438-445 (1989), primary hepatocytes (Ponder et al., Hum. Gene Ther. 2:41-52 (1991), and rodent cells lines and human fibroblast cell lines (van den Wollenberg, Gene 144: 237-241 (1994)).

Generally, there are two types of expression vectors suitable for use in eukaryotic cells, retrovirally-based systems and virion-plasmid hybrids described above. van den Wollenberg et al. describe a retroviral vector that comprises the CMV enhancer genetically engineered within the U3 region of the MPSV promoter. However, retroviral vectors have significant drawbacks for use in industrial level protein production. First, the level of protein production is severely hampered by the retroviral packaging sequence, a necessary component of such vectors, as it interferes with translational initiation. Second, protein production is reduced because the transport of retroviral messenger RNA is less efficient than a standard mRNA and there is competition between retroviral packaging and translation. Third, it is impossible to reach the gene copy numbers routinely achieved by standard vectors with an amplifying selection marker, due to the fact that a retroviral vector implants two promoters for each random integration, thus randomly activating downstream sequences with deleterious effects to the cell. Fourth, there are serious safety concerns with large-scale production of retroviral cultures due to random recombination to replication competency. Finally, retrovirally-established cell lines are harder to document and less efficient to develop since a viral production cell line must first be used to make a master cell bank, then the actual production cell line is produced, requiring a second round of analysis and banking. Accordingly, industrial production of protein is not routinely performed with retroviral vectors.

Thus, the expression of foreign proteins in commercially acceptable quantities remains a challenge. This is especially true in mammalian cell lines. Very often expression of a mammalian protein in a mammalian cell line is required in order to mimic the native form of the protein in all respects: structure, catalytic activity, immunological reactivity, and biological function. Often glycosylation or other post-translational modifications are the key to the production of the desired form of the protein, and bacteria or yeast systems are unable to accomplish these modifications. Thus, there remains a need for improved plasmids that promote the production of mammalian proteins in commercially viable quantities within mammalian host systems.

BRIEF SUMMARY OF THE INVENTION

One aspect of the present invention is a non-retroviral expression vector comprising a cytomegalovirus (CMV) enhancer and a myeloproliferative sarcoma virus (MPSV) promoter. Preferably, the CMV enhancer is located upstream from the 5' end of the MPSV promoter. Most preferably, the CMV enhancer and MPSV promoter construct comprises the polynucleotide sequence of SEQ ID NO:1.

The vector of the present invention can further comprise at least one additional element selected from the group consisting of a consensus Ig intron, a tPA pre-proleader sequence, a polio IRES, a Δ CD8 selection marker, and a human growth hormone polyA signal sequence. Preferably, the vector comprises a consensus Ig intron, a tPA pre proleader sequence, and a polio IRES. The vector can also comprise a structural gene, such as prethrombin.

A further aspect of the present invention is a mammalian cell transfected with the vector. The mammalian cell of the present invention is preferably a CHO cell, and most preferably a CHO of the strain DXB11. The present invention also encompasses a method of producing a recombinant protein comprising transfecting a mammalian host cell with the vector of the present invention, growing the cells under conditions that selectively propagates those cells that have integrated the vector into its genome, and growing the cells with the integrated vector under conditions that cause the recombinant protein to be secreted into the cell medium, and isolating the recombinant protein from the cell medium.

BRIEF DESCRIPTION OF THE FIGURES

FIG. 1 shows a plasmid map containing the MPSV/CMV promoter/enhancer of the present invention. Clockwise the plasmid contains the CMV enhancer, the MPSV LTR promoter minus the negative signal sequence, a consensus Ig intron, a tPA pre-pro leader, polio IRES, a Δ CD8 selection marker, a human growth hormone (hGH) polyA sequence, a dihydrofolate reductase (DHFR) selection cassette with the SV40 promoter/enhancer and SV40 polyA, pUC ori, β lactamase selection, yeast CEN/ARS and URA3 selection. This vector has been named pZMP21.

DESCRIPTION OF THE INVENTION

The present invention fills this need by providing for a novel non-retroviral expression vector, which is able to transfect mammalian cell lines such as Chinese Hamster Ovary Cells (CHO cells) and promote the production of foreign proteins in unexpectedly high quantities. The plasmid of the present invention is comprised of a cytomegalovirus enhancer upstream from the 5' end of a myeloproliferative sarcoma virus (MPSV) promoter. Preferably the MPSV promoter is fused to a cytomegalovirus (CMV) enhancer.

1. Overview

SEQ ID NO: 1 shows a CMV enhancer/MPSV LTR promoter construct of the present invention. The CMV enhancer extends from nucleotide 1 to and including nucleotide 374 of SEQ ID NO: 1. The MPSV LTR promoter extends from nucleotide 375 to and including nucleotide 851.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally occurring nucleotides (such as DNA and RNA), or analogs of naturally occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements [DSEs; McGehee et al., *Mol. Endocrinol*. 7:551 (1993)], cyclic AMP response elements (CREs), serum response elements [SREs; Treisman, *Seminars in Cancer Biol*. 1:47 (1990)], glucocorticoid response elements (GREs), and binding sites for other transcription factors, such as CRE/ATF [O'Reilly et al., *J. Biol. Chem.* 267:19938 (1992)], AP2 [Ye et al., *J. Biol. Chem.* 269:25728 (1994)], SP1, cAMP response element binding protein [CREB; Loeken, *Gene Expr.* 3:253 (1993)] and octamer factors [see, in general, Watson et al., eds., *Molecular Biology of the Gene*, 4th ed. (The Benjamin/Cummings Publishing Company, Inc. 1987), and Lemaigre and Rousseau, *Biochem. J.* 303:1 (1994)]. If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter or increases the translation of the mRNA product that results from transcription driven by the core promoter. For example, a regulatory element may contain a nucleotide sequence that binds with cellular factors that increases transcription over basal levels or imparts transcription exclusively or preferentially in particular cells, tissues, or organelles. Other regulatory elements increase translation of the mRNA message that results because of sequences that are now included in the message, such as an IRES (due to increased ribosome entry) or a poly-A tail (due to increased mRNA stability).

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "non-retroviral vector expression vector" is an expression vector that does not contain a polynucleotide sequence encoding a retroviral packaging element.

A "recombinant host" is a cell that contains a heterologous nucleic acid molecule, such as a cloning vector or expression vector. "Integrative transformants" are recombinant host cells, in which heterologous DNA has become integrated into the genomic DNA of the cells.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal or N-terminal" and "carboxyl-terminal or C-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ $M^{-1}$.

"Upstream" and "downstream" are terms used to describe the relative orientation between two elements present in a nucleotide sequence. An element that is "upstream" of another is located in a position closer to the 5' end of the sequence (i.e., closer to the end of the molecule that has a phosphate group attached to the 5' carbon of the ribose or deoxyribose backbone if the molecule is linear) than the other element. An element is said to be "downstream" when it is located in a position closer to the 3' end of the sequence (i.e., the end of the molecule that has an hydroxyl group attached to the 3' carbon of the ribose or deoxyribose backbone in the linear molecule) when compared to the other element.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

Due to the imprecision of standard analytical methods, molecular weights and lengths of polymers are understood to be approximate values. When such a value is expressed as "about" X or "approximately" X, the stated value of X will be understood to be accurate to ±10%.

Polynucleotides, generally a cDNA sequence, of the present invention encode the described polypeptides herein. A cDNA sequence which encodes a polypeptide of the present invention is comprised of a series of codons, each amino acid residue of the polypeptide being encoded by a codon and each codon being comprised of three nucleotides. The amino acid residues are encoded by their respective codons as follows.

Alanine (Ala) is encoded by GCA, GCC, GCG or GCT;
Cysteine (Cys) is encoded by TGC or TGT;
Aspartic acid (Asp) is encoded by GAC or GAT;
Glutamic acid (Glu) is encoded by GAA or GAG;
Phenylalanine (Phe) is encoded by TTC or TTT;
Glycine (Gly) is encoded by GGA, GGC, GGG or GGT;
Histidine (His) is encoded by CAC or CAT;
Isoleucine (Ile) is encoded by ATA, ATC or ATT;
Lysine (Lys) is encoded by AAA, or AAG;
Leucine (Leu) is encoded by TTA, TTG, CTA, CTC, CTG or CTT;
Methionine (Met) is encoded by ATG;
Asparagine (Asn) is encoded by AAC or AAT;
Proline (Pro) is encoded by CCA, CCC, CCG or CCT;
Glutamine (Gln) is encoded by CAA or CAG;
Arginine (Arg) is encoded by AGA, AGG, CGA, CGC, CGG or CGT;
Serine (Ser) is encoded by AGC, AGT, TCA, TCC, TCG or TCT;
Threonine (Thr) is encoded by ACA, ACC, ACG or ACT;
Valine (Val) is encoded by GTA, GTC, GTG or GTT;
Tryptophan (Trp) is encoded by TGG; and
Tyrosine (Tyr) is encoded by TAC or TAT.

It is to be recognized that according to the present invention, when a polynucleotide is claimed as described herein, it is understood that what is claimed are both the sense strand, the anti-sense strand, and the DNA as double-stranded having both the sense and anti-sense strand annealed together by their respective hydrogen bonds. Also claimed is the messenger RNA (mRNA) that encodes the polypeptides of the president invention, and which mRNA is encoded by the cDNA described herein. Messenger RNA (mRNA) will encode a polypeptide using the same codons as those defined herein, with the exception that each thymine nucleotide (T) is replaced by a uracil nucleotide (U).

3. Detailed Description

The vector of the present invention can be used to produce polypeptides having value in industry, therapeutics, diagnostics, or research. Illustrative proteins include antibodies and antibody fragments, receptors, immunomodulators, hormones, and the like. For example, the expression vector can include a nucleic acid molecule that encodes a pharmaceutically active molecule, such as prethrombin, Factor VIIa, proinsulin, insulin, follicle stimulating hormone, tissue type plasminogen activator, tumor necrosis factor, interleukins (e.g., interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, and IL-19), colony stimulating factors (e.g., granulocyte-colony stimulating factor, and granulocyte macrophage-colony stimulating factor), inteiferons (e.g., interferons-$\alpha$, -$\beta$, -$\gamma$, -$\omega$, -$\delta$, -$\tau$ and -$\epsilon$), a stem cell growth factor, erythropoietin, and thrombopoietin. Additional examples of a protein of interest include an antibody, an antibody fragment, an anti-idiotype antibody (or, fragment thereof), a chimeric antibody, a humanized antibody, an antibody fusion protein, and the like. An example of such an antibody fusion protein would be a fusion of the extracellular portion of the transmembrane activator and CAML-interactor (TACI) protein, such as amino acids 30-110, fused to the Fc portion of human IgG1. The Fc portion can be the native sequence, or one that has been mutated to remove the immunoglobulin effector functions. Examples of these mutations include changes at amino acids 234, 235, 237, 330 and 331 of the IgG1 Fc sequence.

The vectors of the present invention have been found to produce these proteins of interest at higher than expected levels. Without being bound by theory, it is anticipated that the greater than average protein expression displayed by the vectors of the present invention is due, at least in part, to the greater than average stability of expression exhibited by this vector when integrated into the genome of a mammalian host cell.

The gene of interest can be isolated from genomic or cDNA sequences using methods well known to one of ordinary skill or chemically synthesized. If chemically synthesized and double stranded DNA is required, then each complementary strand is made separately. The production of short genes (60 to 80 base pairs) is technically straightforward and can be accomplished by synthesizing the complementary strands and then annealing them. For the production of longer genes (>300 base pairs), however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length.

One method for building a synthetic gene requires the initial production of a set of overlapping, complementary oligonucleotides, each of which is between 20 to 60 nucleotides long. The sequences of the strands are planned so that, after annealing, the two end segments of the gene are aligned to give blunt ends. Each internal section of the gene has complementary 3' and 5' terminal extensions that are designed to base pair precisely with an adjacent section. Thus, after the gene is assembled, the only remaining requirement to complete the process is to seal the nicks along the backbones of the two strands with T4 DNA ligase. In addition to the protein coding sequence, synthetic genes can be designed with terminal sequences that facilitate insertion into a restriction endonuclease sites of a cloning vector and other sequences should also be added that contain signals for the proper initiation and termination of transcription and translation.

An alternative way to prepare a full-size gene is to synthesize a specified set of overlapping oligonucleotides (40 to 100 nucleotides). After the 3' and 5' extensions (6 to 10 nucleotides) are annealed, large gaps still remain, but the base-paired regions are both long enough and stable enough to hold the structure together. The duplex is completed and the gaps filled by enzymatic DNA synthesis with *E. coli* DNA polymerase I. This enzyme uses the 3'-hydroxyl groups as replication initiation points and the single-stranded regions as templates. After the enzymatic synthesis is completed, the nicks are sealed with T4 DNA ligase. For larger genes, the complete gene sequence is usually assembled from double-stranded fragments that are each put together by joining four to six overlapping oligonucleotides (20 to 60 base pairs each). If there is a sufficient amount of the double-stranded fragments after each synthesis and annealing step, they are simply joined to one another. Otherwise, each fragment is cloned into a vector to amplify the amount of DNA available. In both cases, the double-stranded constructs are sequentially linked to one another to form the entire gene sequence. Each double-stranded fragment and the complete sequence should be characterized by DNA sequence analysis to verify that the chemically synthesized gene has the correct nucleotide sequence. For reviews on polynucleotide synthesis, see, for example, Glick and Pasternak, *Molecular Biotechnology, Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

Expression vectors that are suitable for production of an amino acid sequence of interest in eukaryotic cells typically contain (1) eukaryotic or viral DNA elements that control initiation and level of transcription, such as a promoter and an enhancer; (2) DNA elements that control the processing of transcripts, such as a transcription termination/polyadenylation sequence; and (3) one or more selectable marker gene(s) and other sequences useful for stable gene expression for all anticipated host cells. Expression vectors can also include nucleotide sequences encoding a secretory sequence that directs the heterologous polypeptide into the secretory pathway of a host cell.

To express a gene of interest or a selectable marker gene, a nucleic acid molecule encoding the amino acid sequence must be operably linked to regulatory sequences that control transcriptional expression and then, introduced into a host cell. The vector of the present invention comprises the MPSV promoter with the CMV enhancer in a 5' position to the promoter. MPSV is a member of the Moloney murine sarcoma virus family (Mo-MuSV) and can transform fibroblasts in vitro and cause sarcoma in vivo. Additionally, MPSV causes an acute myeloproliferative disease in adult mice. The mos oncogene, which is a component of the virus genome, is necessary for the virus' transforming function, but it is sequences specific to its long terminal repeat (LTR) that account for expanded cell target specificity when compared to Mo-MuSV. These additional cell targets makes the MPSV LTR an attractive promoter for mammalian cell line expression. The MPSV LTR is generally defined as nucleotides between −416 to +31 in relation to the transcription initiation site located within the LTR sequences, although other sequences of the MPSV LTR that function as a promoter can also be used. Preferably, the MPSV promoter has the sequence of nucleotides 375 to 851 of SEQ ID NO: 1. The MPSV LTR includes sequences that have been identified as negatively controlling transcription. Although deletion of these sequences proved to have marginal effect on protein production, so they remain in pZMP21, they can optionally be deleted in the vector of the present invention.

The second regulatory element of the present invention is the CMV enhancer and can be generally defined as the nucleotides between −118 and −524 5' of the transcription initiation site of the major immediate-early gene of CMV. Preferably, the CMV enhancer has the sequence of nucletodes 1 to 374 of SEQ ID NO: 1. The enhancer function of this fragment of the viral genome was discovered based on its ability to produce recombinant viruses when cotransfected with enhancerless SV40 viral genome (Boshart et al., Cell, 41 (2):521-30 (1985)). For the vectors of the present invention, this sequence, or functionally fragments thereof, is placed within the vector such that an increase in transcription results when compared to the transcription without the presence of the CMV enhancer. Preferably, this location is 5' of the MPSV promoter sequence.

The vector of the present invention can comprise other regulatory elements that can increase the expression of the recombinant protein of interest within mammalian host cells. Among the other regulatory elements that can be included is the transcription enhancer located within the intron of an immunoglobulin gene. Particularly preferred is a consensus Ig intron sequence that comprises sequences that have been optimized for use in mammalian host cells such as CHO DXB11. A second additional regulatory element is an internal ribosome entry site (IRES), a sequence derived from viral genomes that allows for the translation of a dicistronic message. Particularly preferred is the IRES derived from the polio virus. A third regulatory element is a poly-A signal sequence that results in the addition of adenosine residues on the end of the mRNA message, which increases the message stability. Particularly preferred is the poly-A signal sequence derived from the human growth hormone (hGH) gene sequence.

Recombinant host cells can be produced that secrete the amino acid sequence of interest into surrounding medium. Accordingly, the present invention contemplates expression vectors comprising a nucleotide sequence that encodes a secretory signal sequence, which is also known as a "signal peptide," a "leader sequence," a "prepro sequence," or a "pre sequence." The secretory signal sequence is operably linked to a gene of interest such that the two sequences are joined in the correct reading frame and positioned to direct the newly synthesized polypeptide of interest into the secretory pathway of the host cell. Secretory signal sequences are commonly positioned 5' to the nucleotide sequence encoding the amino acid sequence of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830). The present invention can utilize a tissue plasminogen activator (tPA) pre-proleader derived from the sequence described in U.S. Pat. No. 5,641,655. Mutations have been introduced into the pre-proleader so that it is optimized for use within mammalian expression systems.

Expression vectors can also comprise nucleotide sequences that encode a peptide tag to aid the purification of the polypeptide of interest. Peptide tags that are useful for isolating recombinant polypeptides include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

A wide variety of selectable marker genes for use in mammalian expression vectors are available (see, for example, Kaufman, *Meth. Enzymol.* 185:487 (1990); Kaufman, *Meth. Enzymol.* 185:537 (1990)). Selectable marker genes generally confer growth resistance to a chemical or drug, that allow selection of initial positive transformants in bacterial, yeast, or mammalian host cells. Selectable markers fall into two functional categories: recessive and dominant. The recessive markers are usually genes that encode products that are not produced in the host cells, i.e., host cells that lack the "marker" product or function. Marker genes for thymidine kinase (TK), dihydrofolate reductase (DHFR), adenine phosphoribosyl transferase (APRT), and hypoxanthine-guanine phosphoribosyl transferase (HGPRT) are in this category. (see, for example, Srivastava and Schlessinger, *Gene* 103:53 (1991); Romanos et al., "Expression of Cloned Genes in Yeast," in *DNA Cloning 2: Expression Systems*, 2$^{nd}$ Edition, pages 123-167 (IRL Press 1995); Markie, *Methods Mol. Biol.* 54:359 (1996); Pfeifer et al., *Gene* 188:183 (1997); Tucker and Burke, *Gene* 199:25 (1997); Hashida-Okado et al., *FEBS Letters* 425:117 (1998)).

Dominant markers include genes that encode products that confer resistance to growth-suppressing compounds (such as antibiotics or other drugs) and/or permit growth of the host cells in metabolically restrictive environments. Commonly used markers within this category include a. mutant DHFR gene that confers resistance to methotrexate; the gpt gene for xanthine-guanine phosphoribosyl transferase, which permits host cell growth in mycophenolic acid/xanthine containing media; and the neo gene for aminoglycoside 3'-phosphotransferase, which can confer resistance to G418, gentamycin, kanamycin, and neomycin. More newly developed markers include resistance to zeocin, bleomycin, blasticidin, and hygromycin (see, e.g., Gatignol et al., *Mol. Gen. Genet.* 207:342 (1987); Drocourt et al., *Nucl. Acids Res.* 18:4009 (1990)).

The use of selectable markers has been extended beyond isolation of cells that have incorporated the vector sequences to selection for cells that are expressing the recombinant protein at a high level. An example of this selection process is co-expression of green fluorescent protein with the recombinant protein. The use of autofluorescent proteins provides a visual mechanism to assess if host cells are overexpressing recombinant protein. Similar selection can be performed with a cell surface protein that can be detected with an antibody (e.g. CD4, CD8, Class I major histocompatibility complex (MHC) protein, etc.). Preferably, the cytoplasmic domain of the cell surface protein has been deleted, in order to reduce the cytological effect on the host cell of overexpression of the protein. The expression products of such selectable marker genes can be used to sort transfected cells from untransfected cells by such standard means as FACS sorting or magnetic bead separation technology. Selectable marker genes can be cloned or synthesized using published nucleotide sequences, or marker genes can be obtained commercially.

The present vector preferably utilizes as selectable makers a DHFR cassette with the SV40 promoter/enhancer for use in mammalian host cells, a CD8 Δ construct (Δ indicating that the sequence encoding the cytoplasmic domain of the protein has been deleted) to determine recombinant gene expression at the cell surface of mammalian cells, β lactamase for use in bacterial host cells, and URA3 for use in yeast host cells.

A final common component of expression vectors are sequences that facilitate the replication of the vector in mammalian, yeast, and bacterial hosts such as centromeres, origins of replication, chromatin stability sequences, and the like, that increase the stability of the vector in the host system. For example, the vector of present invention can comprise the pUC origin of replication for use in bacterial host cells and the *S. cerevisiae* CEN/ARS origin of replication for use in yeast host cells. Chromatin elements that may modulate protein expression levels and/or stability are: locus control regions (LCR), matrix or scaffold attachment regions (MAR or SAR) or insulators.

Both during and after construction of the expression vector comprising the amino acid-encoding sequences of interest, the vector is typically propagated in a host cell. Vector propagation can be carried out in a prokaryotic host cell, such as *E. coli*. Suitable strains of *E. coli* include BL21(DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Standard techniques for propagating vectors in prokaryotic hosts are well-known to those of skill in the art (see, for example, Ausubel et al. (eds.), *Short Protocols in Molecular Biology*, 3$^{rd}$ Edition (John Wiley & Sons 1995) ["Ausubel 1995"]; Wu et al., *Methods in Gene Biotechnology* (CRC Press, Inc. 1997)).

Alternatively, vector propagation both during or after vector construction can be carried out in eukaryotic cells, such as yeast. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillennondii* and *Candida maltosa* are known in the art. See, for example, Gleeson et al., *J. Gen. Microbiol.* 132:3459 (1986), and Cregg, U.S. Pat. No. 4,882,279.

Ultimately, the amino acid sequence of interest may be expressed in any prokaryotic or eukaryotic host cell as described above. Preferably, using the vector of the present invention, the amino acid sequence of interest is produced by a eukaryotic cell, such as a mammalian cell. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44; CHO DXB11 (Hyclone, Logan, Utah); see also, e.g., Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658). The CHO strain DXB11is the preferred host cell for protein production utilizing the vector of the present invention.

An expression vector can be introduced into host cells using a variety of standard techniques including calcium phosphate transfection, liposome-mediated transfection, microprojectile-mediated delivery, electroporation, and the like. Transfected cells can be selected and propagated to provide recombinant host cells that comprise the gene of interest stably integrated in the host cell genome. Standard methods for introducing nucleic acid molecules into bacterial, yeast, insect, mammalian, and plant cells are provided, for example, by Ausubel (1995). General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996).

The present invention, thus generally described, will be understood more readily by reference to the following examples, which are provided by way of illustration and are not intended to be limiting of the present invention.

EXAMPLE 1

Construction of MPSV Promoter and pZMP21

The MPSV LTR promoter was constructed synthetically by assembling oligonucleotides in sets of four using PCR.

First the oligos were assembled in pairs by PCR:SEQ ID NOs: 4+5, 6+7, 8+9, 10+11, 12+13, 14+15. Then the pairs were assembled into three sets of four oligos SEQ ID NOS: 4+5 and 6+7, with oligos SEQ ID NOs: 4 and 7 as primers, 8+9 and 10+11 with oligos 8 and 11 as primers, and 12+13 and 14+15 with oligos 12 and 15 as primers in PCR reactions. When the three PCR fragments were assembled a smaller than expected product was observed. A new primer, 16, was made to get around the internal repeat that lead to this deletion. The product of 4+7 was, extended with primers 4 and 16 to make a better overlap with the product of 8+15. 4+16 and 8+15 were assembled with primers 4 and 15 by PCR to make a full length product.

The PCR reactions were run as follows: to a 100 µl final volume was added, 10 µl 10×Taq polymerase Reaction Buffer (Perkin Elmer), 8 µl of 2.5 mM dNTPs, 78 µl dH$_2$O, 2 µl each of a 20 mM stock solution of the two primers described above, and taq polymerase (2.5 units, Life Technology). An equal volume of mineral oil was added and the reaction was heated to 94° C. for 2 minutes, followed by 25 cycles at 94° C. for 30 seconds, 45° C. for 30 seconds, 72° C. for 30 seconds followed by a 5 minute extension at 72° C. In the case of the first stage of assembly the primers were also the templates of the reaction. For the later steps, 10 µl of PCR product was used as template for the each level of assembly.

Ten µl of the 100 µl PCR reaction is run on a 1.0% agarose gel with 1×TBE buffer for analysis. The remaining 90 µl of PCR reaction is precipitated with the addition of 5 µl 1 M NaCl and 250 µl of absolute ethanol. The plasmid pZMP20 which has been cut with NheI is used for recombination with the PCR fragment. Plasmid pZMP20 was constructed from pZP9 (deposited at the American Type Culture Collection, 10801 University Boulevard, Manassas, Va. 20110-2209, and is designated No. 98668) with the yeast genetic elements taken from pRS316 (deposited at the American Type Culture Collection, 10801 University Boulevard, Manassas, Va. 20110-2209, and designated No. 77145), an IRES element from poliovirus, and the extracellular domain of CD8, truncated at the carboxyl terminal end of the transmembrane domain. pZMP20 is a mammalian expression vector containing an expression cassette having the cytomegalovirus immediate early promoter, immunoglobulin signal peptide intron, multiple restriction sites for insertion of coding sequences, a stop codon and a human growth hormone terminator. The plasmid also has an *E. coli* origin of replication, a mammalian selectable marker expression unit having an SV40 promoter, enhancer and origin of replication, a DHFR gene, the SV40 terminator, as well as the URA3 and CEN-ARS sequences required for selection and replication in *S. cerevisiae*.

One hundred microliters of competent yeast cells (*S. cerevisiae*) are independently combined with 10 µl of the various DNA mixtures from above and transferred to a 0.2 cm electroporation cuvette. The yeast/DNA mixtures are electropulsed at 0.75 kV (5 kV/cm), ∞ ohms, 25 µF. To each cuvette is added 600 µl of 1.2 M sorbitol and the yeast is plated in two 300 µl aliquots onto two URA-D plates and incubated at 30° C. After about 48 hours, the Ura+ yeast transformants from a single plate are resuspended in 1 ml H$_2$O and spun briefly to pellet the yeast cells. The cell pellet is resuspended in 1 ml of lysis buffer (2% Triton X-100, 1% SDS, 100 mM NaCl, 10 mM Tris, pH 8.0, 1 mM EDTA). Five hundred microliters of the lysis mixture is added to an Eppendorf tube containing 300 µl acid washed glass beads and 200 µl phenol-chloroform, vortexed for 1 minute intervals two or three times, followed by a 5 minute spin in a Eppendorf centrifuge at maximum speed. Three hundred microliters of the aqueous phase is transferred to a fresh tube, and the DNA precipitated with 600 µl ethanol (EtOH), followed by centrifugation for 10 minutes at 4° C. The DNA pellet is resuspended in 10 µl H$_2$O.

Transformation of electrocompetent *E. coli* cells (DH10B, GibcoBRL) is done with 0.5-2 ml yeast DNA prep and 40 ul of DH10B cells. The cells are electropulsed at 1.7 kV, 25 µF and 400 ohms. Following electroporation, 1 ml SOC (2% Bacto' Tryptone (Difco, Detroit, Mich.), 0.5% yeast extract (Difco), 10 mM NaCl, 2.5 mM KCl, 10 mM MgCl2, 10 mM MgSO4, 20 mM glucose) is plated in 250 µl aliquots on four LB AMP plates (LB broth (Lennox), 1.8% Bacto Agar (Difco), 100 mg/L Ampicillin).

Individual clones harboring the correct construct are identified by restriction digest to verify the presence of the MPSV promoter and to confirm that the various DNA sequences have been joined correctly to one another. The insert of positive clones are subjected to sequence analysis. Larger scale plasmid DNA is isolated using the Qiagen Maxi kit (Qiagen) according to manufacturer's instruction. pZMP21 was deposited on Jun. 17, 2003 at the American Type Culture Collection (ATCC) 10801 University Boulevard, Manassas, Va. 20110-2209, designated as ATCC#PTA-5266.

EXAMPLE 2

Construction of Prethrombin Expression Vectors

An expression plasmid containing all or part of a polynucleotide encoding prethrombin is constructed via homologous recombination. A fragment of prethrombin cDNA is isolated using PCR that includes the polynucleotide sequence from nucleotide 1 to nucleotide 1380 of SEQ ID NO: 15 with flanking regions at the 5' and 3' ends corresponding to the vectors sequences flanking the prethrombin insertion point. The primers for PCR each include from 5' to 3' end: 40 bp of flanking sequence from the vector and 17 bp corresponding to the amino and carboxyl termini from the open reading frame of prethrombin.

Ten μl of the 100 μl PCR reaction is run on a 0.8% LMP agarose gel (Seaplaque GTG) with 1×TBE buffer for analysis. The remaining 90 μl of PCR reaction is precipitated with the addition of 5 μl 1 M NaCl and 250 μl of absolute ethanol. The plasmids pZMP20 and pZMP21, described in the previous example, which were cut with BglII were used for recombination with the PCR fragment.

One hundred microliters of competent yeast cells (*S. cerevisiae*) are independently combined with 10 μl of the various DNA mixtures from above and transferred to a 0.2 cm electroporation cuvette. The yeast/DNA mixtures are electropulsed at 0.75 kV (5 kV/cm), ∞ ohms, 25 μF. To each cuvette is added 600 μl of 1.2 M sorbitol and the yeast is plated in two 300 μl aliquots onto two URA-D plates and incubated at 30° C. After about 48 hours, the Ura+ yeast transformants from a single plate are resuspended in 1 ml H$_2$O and spun briefly to pellet the yeast cells. The cell pellet is resuspended in 1 ml of lysis buffer (2% Triton X-100, 1% SDS, 100 mM NaCl, 10 mM Tris, pH 8.0, 1 mM EDTA). Five hundred microliters of the lysis mixture is added to an Eppendorf tube containing 300 μl acid washed glass beads and 200 μl phenol-chloroform, vortexed for 1 minute intervals two or three times, followed by a 5 minute spin in a Eppendorf centrifuge at maximum speed. Three hundred microliters of the aqueous phase is transferred to a fresh tube, and the DNA precipitated with 600 μl ethanol (EtOH), followed by centrifugation for 10 minutes at 4° C. The DNA pellet is resuspended in 10 μl H$_2$O.

Transformation of electrocompetent *E. coli* cells (DH10B, Invitrogen) is done with 0.5-2 ml yeast DNA prep and 40 ul of DH10B cells. The cells are electropulsed at 1.7 kV, 25 μF and 400 ohms. Following electroporation, 1 ml SOC (2% Bacto' Tryptone (Difco, Detroit, Mich.), 0.5% yeast extract (Difco), 10 mM NaCl, 2.5 mM KCl, 10 mM MgCl2, 10 mM MgSO4, 20 mM glucose) is plated in 250 μl aliquots on four LB AMP plates (LB broth (Lennox), 1.8% Bacto Agar (Difco), 100 mg/L Ampicillin).

Individual clones harboring the correct expression construct for prethrombin are identified by restriction digest to verify the presence of the prethrombin insert and to confirm that the various DNA sequences have been joined correctly to one another. The insert of positive clones are subjected to sequence analysis. Larger scale plasmid DNA is isolated using the Qiagen Maxi kit (Qiagen) according to manufacturer's instruction.

EXAMPLE 3

Expression of Prethrombin in Protein-free, Suspension-adapted CHO Cells

Serum-free, suspension-adapted CHO DG44 cells were electroporated with two of the plasmids described above: pZMP21-prethrombin and the control plasmid, pZMP20-prethrombin, by the following method. The plasmids were linearized by digestion with PvuI, precipitated with sodium acetate and ethanol then rinsed with 70% ethanol and dried. The pellets were resuspended at a concentration of 200 μg/100 μl per electroporation in PFCHO medium supplemented with 4 mM L-Glut, 1% Hypoxanthine/Thymidine, 1% vitamins, and 1% Na pyruvate (Invitrogen). Cells, growing at log phase, were pelleted and resuspended at 5E6/800 μl per electroporation reaction. The electroporation was performed in a BioRad GenePulser II with Capacitance extender (BioRad, Hercules, Calif.), at 300 v and 950 μFd in 4 mm cuvettes. The cells were suspended in 25 ml of the medium described above in 125 mL shake flasks and put on shakers in cell culture incubators at 37° C., at 80 rpm for 24 h to recover. The cells were then pelleted and resuspended at 2.5E5 in selective medium, consisting of PFCHO supplemented with 4 mM L-Glut, 1% vitamins, 1% Na Pyruvate. Cell lines were further cultured in increasing concentrations of methotrexate up to 1 μM once the cultures were capable of growing in the absence of hypoxanthine/thymidine supplementation. Once the cultures were growing actively in selection media and the viability had increased to over 95%, cultures were established for harvest and analysis of protein. Cultures were seeded at 5E5/mL at 25 mL in shake flasks, and allowed to grow for 48 h then harvested. The supernatants were filtered through 0.22 μm filters and analyzed by ELISA assay.

Figure 1:
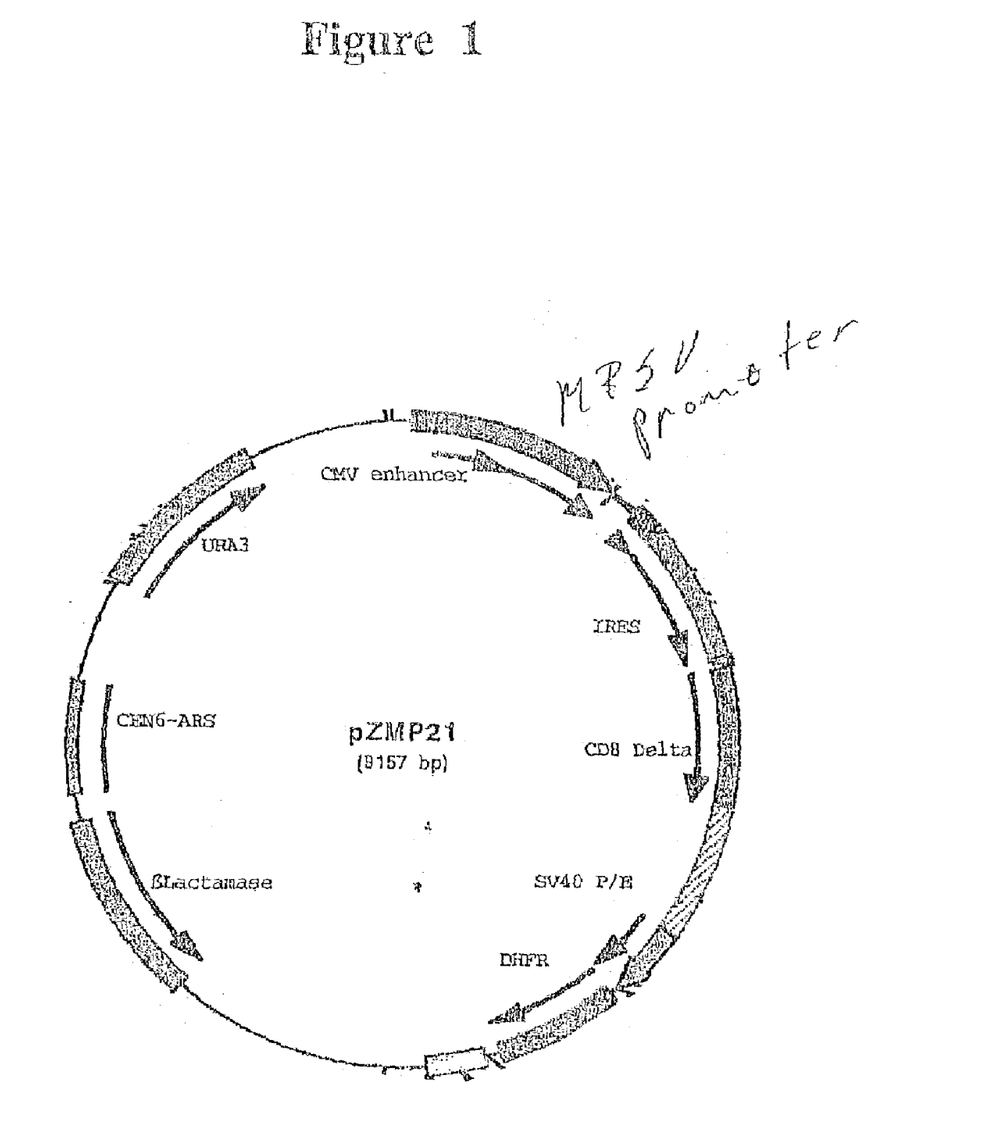
Figure 2:
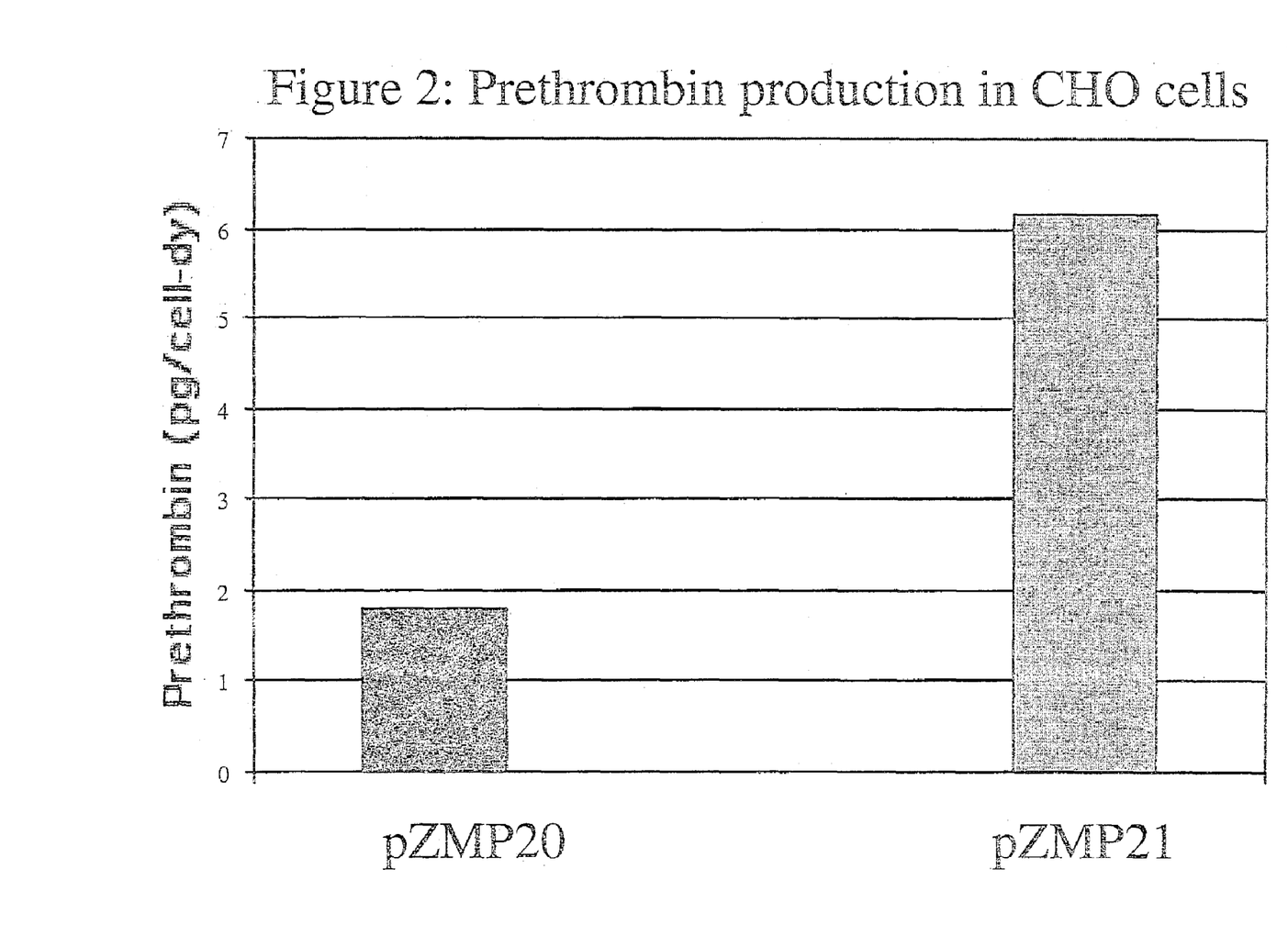
FIG. 2 compares the picograms per cell per day (pg/cell-day) of prethrombin production for Chinese Hamster Ovary (CHO) cells transfected with pZMP20 (CMV promoter/enhancer) or pZMP21 (MPSV promoter/CMV enhancer).

The ELISA assay was performed using two polyclonal antibodies: capture antibody, sheep anti-human prethrombin fragment 2 (Accurate Chemical #20112AP) and detection antibody, sheep anti-human prethrombin-HRP conjugate (Accurate Chemical #20110HP). The coating antibody was diluted in 0.1 M Na carbonate pH 9.6 at 1 μg/mL, dispensed into 96 wells and incubated at 4° C. overnight. The plates were rinsed five times in wash buffer (PBS plus 0.05% Tween) and blocked by incubating twices with SuperBlock (Pierce, Rockford, Ill., #37515) 200 μl/well 5 minutes at room temperature. The samples and standards were applied to the plate in binding buffer (PBS, 0.05% Tween, 1 mg/mL BSA) and incubated 1 hour at 37° C. The plates were washed five times in wash buffer and detection antibody diluted to 2 ng/mL in binding buffer. The detection antibody was applied to the wells and incubated 1 h at 37° C. The plates were rinsed five times with wash buffer and the detection reagent, OPD, was applied. OPD was prepared by adding hydrogen peroxide immediately before use according to the manufacturer's instructions (Pierce, Rockford, Ill. #34006), 100 μl added to each well, allowed to develop 10 minutes at RT and stopped with 100 μl per well of 1 N H2SO4. Plates were read at 492 nm. The results were calculated via SoftMaxPro. Production rates of prethrombin by CHO cell pools was calculated by dividing the prethrombin titer by the average number of cells and the number of days in culture. These comparative results are shown in a bar graph in FIG. 2 and indicate that pZMP21-prethrombin produces approximately 3.6 times the amount of recombinant protein as the pZMP20-prethrombin control.

EXAMPLE 4

Construction of zsig37 Expression Vectors

An expression plasmid containing all or part of a polynucleotide encoding zsig37 is constructed via homologous recombination. A fragment of zsig37 cDNA is isolated using PCR that includes the polynucleotide sequence from nucleotide 1 to nucleotide 873 of SEQ ID NO: 16 with flanking regions at the 5' and 3' ends corresponding to the vectors sequences flanking the zsig37 insertion point. The primers for PCR each include from 5' to 3' end: 40 bp of flanking sequence from the vector and 17 bp corresponding to the amino and carboxyl termini from the open reading frame of zsig37.

Ten µl of the 100 µl PCR reaction is run on a 0.8% LMP agarose gel (Seaplaque GTG) with 1×TBE buffer for analysis. The remaining 90 µl of PCR reaction is precipitated with the addition of 5 µl 1 M NaCl and 250 µl of absolute ethanol. The plasmids pZMP20 and pZMP21, described in the previous example, which were cut with BglII were used for recombination with the PCR fragment.

One hundred microliters of competent yeast cells (*S. cerevisiae*) are independently combined with 10 µl of the various DNA mixtures from above and transferred to a 0.2 cm electroporation cuvette. The yeast/DNA mixtures are electropulsed at 0.75 kV (5 kV/cm), ∞ ohms, 25 µF. To each cuvette is added 600 µl of 1.2 M sorbitol and the yeast is plated in two 300 µl aliquots onto two URA-D plates and incubated at 30° C. After about 48 hours, the Ura+ yeast transformants from a single plate are resuspended in 1 ml $H_2O$ and spun briefly to pellet the yeast cells. The cell pellet is resuspended in 1 ml of lysis buffer (2% Triton X-100, 1% SDS, 100 mM NaCl, 10 mM Tris, pH 8.0, 1 mM EDTA). Five hundred microliters of the lysis mixture is added to an Eppendorf tube containing 300 µl acid washed glass beads and 200 µl phenol-chloroform, vortexed for 1 minute intervals two or three times, followed by a 5 minute spin in a Eppendorf centrifuge at maximum speed. Three hundred microliters of the aqueous phase is transferred to a fresh tube, and the DNA precipitated with 600 µl ethanol (EtOH), followed by centrifugation for 10 minutes at 4° C. The DNA pellet is resuspended in 10 µl $H_2O$.

Transformation of electrocompetent *E. coli* cells (DH10B, Invitrogen) is done with 0.5-2 ml yeast DNA prep and 40 ul of DH10B cells. The cells are electropulsed at 1.7 kV, 25 µF and 400 ohms. Following electroporation, 1 ml SOC (2% Bacto' Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) is plated in 250 µl aliquots on four LB AMP plates (LB broth (Lennox), 1.8% Bacto Agar (Difco), 100 mg/L Ampicillin).

Individual clones harboring the correct expression construct for zsig37 are identified by restriction digest to verify the presence of the zsig37 insert and to confirm that the various DNA sequences have been joined correctly to one another. The insert of positive clones is subjected to sequence analysis. Larger scale plasmid DNA is isolated using the Qiagen Maxi kit (Qiagen) according to manufacturer's instruction.

EXAMPLE 5

Analysis of the Stability of Production of zsig37 by Cells Transfected with MPSV vs. CMV Expression Vectors Serum-free, suspension-adapted CHO DG44 cells are electroporated with the plasmids described above, by the following method. The plasmids are linearized by digestion with PvuI, precipitated with sodium acetate and ethanol then rinsed with 70% ethanol and dried. The pellets are resuspended at a concentration of 200 µg/100 µl per electroporation in PFCHO medium supplemented with 4 mM L-Glut, 1% Hypoxanthine/Thymidine, 1% vitamins, and 1% Na pyruvate (Invitrogen). Cells, growing at log phase, are pelleted and resuspended at 5E6/800 µl per electroporation reaction. The electroporation is performed in , at 300 v and 950 µFd in 4 mm cuvettes. The cells are suspended in 25 ml of the medium described above in 125 mL shake flasks and put on shakers in cell culture incubators at 37° C., at 80 rpm for 24 h to recover. The cells are then pelleted and resuspended at 2.5E5 in selective medium, consisting of PFCHO supplemented with 4 mM L-Glut, 1% vitamins, 1% Na Pyruvate. Cell lines are further cultured in increasing concentrations of methotrexate up to 1 µM once the cultures are capable of growing in the absence of hypoxanthine/thymidine supplementation. Once the cultures are growing actively in selection media and the viability has increased to over 95%, cultures are established for harvest and analysis of protein. Cultures are passaged over a period of three months and samples are removed weekly for analysis by ELISA. The supernatants were filtered through 0.22 µm filters and analyzed by ELISA assay.

The ELISA assay is performed using two polyclonal antibodies: capture antibody, sheep anti-human zsig37 and detection antibody, sheep anti-human zsig37-HRP conjugate. The coating antibody is diluted in 0.1 M Na carbonate pH 9.6 at 1 µg/mL, dispensed into 96 wells and incubated at 4° C. overnight. The plates are rinsed five times in wash buffer (PBS plus 0.05% Tween) and blocked by incubating twices with SuperBlock (Pierce, Rockford, Ill., #37515) 200 µl/well 5 minutes at room temperature. The samples and standards are applied to the plate in binding buffer (PBS, 0.05% Tween, 1 mg/mL BSA) and incubated 1 hour at 37° C. The plates are washed five times in wash buffer and detection antibody diluted to 2 ng/mL in binding buffer. The detection antibody is applied to the wells and incubated 1 h at 37° C. The plates are rinsed five times with wash buffer and the detection reagent, OPD, was applied. OPD is prepared by adding hydrogen peroxide immediately before use according to the manufacturer's instructions (Pierce, Rockford, Ill., #34006), 100 µl added to each well, allowed to develop 10 minutes at RT and stopped with 100 µl per well of 1 N $H_2SO_4$. Plates are read at 492 nm. The results are calculated via SoftMaxPro. Production rates of zsig37 by CHO cell pools is calculated by dividing the zsig37 titer by the average number of cells and the number of days in culture. The levels of productivity as a function of time are calculated for the two cultures for comparison.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. The vector pZMP21 as deposited with the ATCC, having the reference number ATCC PTA-5266.

2. The vector of claim 1 further comprises a structural gene such that the gene is operably linked to the cytomegalovirus enhancer and the myeloproliferative sarcoma virus promoter.

3. A mammalian cell transfected with the vector of claim 2.

4. A method of producing a recombinant protein comprising
   a. transfecting a mammalian host cell with the vector of claim 2;
   b. growing the cells under conditions that selectively propagate those cells that have integrated the vector of claim 1 into its genome;
   c. growing the cells of step b) under conditions that cause the recombinant protein to be secreted into the cell medium;
   d. isolating the recombinant protein from the cell medium.

5. A method of producing a recombinant protein comprising
   a. randomly integrating the vector of claim 2 into the genome of CHO cells;
   b. growing the cells in the presence of increasing concentrations of methotrexate;
   c. isolating cells from step b) and growing under conditions such that the CHO cells produce the recombinant protein into the culture medium;
   d. isolating the recombinant protein from the culture medium.

6. The mammalian cell of claim 3 wherein the cell is a CHO cell.

7. The mammalian cell of claim 6 wherein the CHO cell is of strain DXB 11.

8. The method of claim 4 wherein the transfection occurs by electroporation.

9. The method of claim 4 wherein step b) comprises growing the cells in the presence of methotrexate.

10. The method of claim 5 wherein the CHO cells are of the strain DXB 11.

* * * * *

UNITED STATES PATENT AND TRADEMARK OFFICE
CERTIFICATE OF CORRECTION

PATENT NO. : 7,262,025 B2　　　　　　　　　　　　　　　　　　　　　　　Page 1 of 1
APPLICATION NO. : 10/465156
DATED : August 28, 2007
INVENTOR(S) : Margaret Dow Moore It is certified that error appears in the above-identified patent and that said Letters Patent is hereby corrected as shown below:

Column 8, line 39, "inteiferons" should be --interferons--.
Column 13, line 5, "guillennondii" should be --guilliermondii--.
Column 31, line 14, "comprises" should be --comprising--.

Signed and Sealed this

Fourteenth Day of April, 2009

JOHN DOLL
*Acting Director of the United States Patent and Trademark Office*

SEQUENCE LISTING

<160> NUMBER OF SEQ ID NOS: 16

<210> SEQ ID NO 1
<211> LENGTH: 851
<212> TYPE: DNA
<213> ORGANISM: Artificial Sequence
<220> FEATURE:
<223> OTHER INFORMATION: hybrid cytomegalovirus and myeloproliferative
      sarcoma virus regulatory sequence

<400> SEQUENCE: 1

```
ggctgaccgc ccaacgaccc ccgcccattg acgtcaataa tgacgtatgt tcccatagta    60
acgccaatag ggactttcca ttgacgtcaa tgggtggagt atttacggta aactgcccac   120
ttggcagtac atcaagtgta tcatatgcca agtacgcccc ctattgacgt caatgacggt   180
aaatggcccg cctggcatta tgcccagtac atgaccttat gggactttcc tacttggcag   240
tacatctacg tattagtcat cgctattacc atggtgatgc ggttttggca gtacatcaat   300
gggcgtggat agcggtttga ctcacgggga tttccaagtc tccacccat tgacgtcaat   360 gggagtttgt tttgaatgaa agaccccacc tgtaggtttg gcaagctagc ttaagtaacg   420
ccatttgcaa ggcatggaaa atacataac tgagaataga gaagttcaga tcaaggtcag   480
gaacagagaa acaggagaat atgggccaaa caggatatct gtggtaagca gttcctgccc   540
cgctcagggc caagaacagt tggaacagga gaatatgggc caaacaggat atctgtggta   600
agcagttcct gccccgctca gggccaagaa cagatggtcc ccagatcggt cccgccctca   660
gcagtttcta gagaaccatc agatgtttcc agggtgcccc aaggacctga atgaccctg    720 tgccttattt gaactaacca atcagttcgc ttctcgcttc tgttcgcgcg cttctgctcc   780
ccgagctcaa taaaagagcc cacaacccct cactcggcgc gccagtcctc cgatagactg   840
cgtcgcccgg g                                                        851
```

<210> SEQ ID NO 2
<211> LENGTH: 60
<212> TYPE: DNA
<213> ORGANISM: cytomegalovirus

<400> SEQUENCE: 2

```
caagtctcca ccccattgac gtcaatggga gtttgttttg caatgaaaga ccccacctgt    60
```

<210> SEQ ID NO 3
<211> LENGTH: 65
<212> TYPE: DNA
<213> ORGANISM: cytomegalovirus

<400> SEQUENCE: 3

```
ttccatgcct tgcaaatggc gttacttaag ctagcttgcc aaacctacag gtggggtctt    60
tcatt                                                               65
```

<210> SEQ ID NO 4
<211> LENGTH: 63
<212> TYPE: DNA
<213> ORGANISM: cytomegalovirus

<400> SEQUENCE: 4

```
ccatttgcaa ggcatggaaa atacataac tgagaataga gaagttcaga tcaaggtcag    60
gaa                                                                 63
```

<210> SEQ ID NO 5
<211> LENGTH: 63
<212> TYPE: DNA
<213> ORGANISM: cytomegalovirus

<400> SEQUENCE: 5
cttaccacag atatcctgtt tggcccatat tctcctgttt ctctgttcct gaccttgatc    60
tga                                                                 63

<210> SEQ ID NO 6
<211> LENGTH: 64
<212> TYPE: DNA
<213> ORGANISM: cytomegalovirus

<400> SEQUENCE: 6
acaggatatc tgtggtaagc agttcctgcc ccgctcaggg ccaagaacag ttggaacagg    60
agaa                                                                64

<210> SEQ ID NO 7
<211> LENGTH: 64
<212> TYPE: DNA
<213> ORGANISM: cytomegalovirus

<400> SEQUENCE: 7
gagcggggca ggaactgctt accacagata tcctgtttgg cccatattct cctgttccaa    60
ctgt                                                                64

<210> SEQ ID NO 8
<211> LENGTH: 65
<212> TYPE: DNA
<213> ORGANISM: cytomegalovirus

<400> SEQUENCE: 8
agcagttcct gccccgctca gggccaagaa cagatggtcc ccagatcggt cccgccctca    60
gcagt                                                               65

<210> SEQ ID NO 9
<211> LENGTH: 66
<212> TYPE: DNA
<213> ORGANISM: cytomegalovirus

<400> SEQUENCE: 9
atttcaggtc cttggggcac cctggaaaca tctgatggtt ctctagaaac tgctgagggc    60
gggacc                                                              66

<210> SEQ ID NO 10
<211> LENGTH: 65
<212> TYPE: DNA
<213> ORGANISM: cytomegalovirus

<400> SEQUENCE: 10
gccccaagga cctgaaatga ccctgtgcct tatttgaact aaccaatcag ttcgcttctc    60
gcttc                                                               65

<210> SEQ ID NO 11
<211> LENGTH: 67
<212> TYPE: DNA
<213> ORGANISM: cytomegalovirus

<400> SEQUENCE: 11

```
ggggttgtgg gctctttat tgagctcggg gagcagaagc gcgcgaacag aagcgagaag    60
cgaactg                                                             67

<210> SEQ ID NO 12
<211> LENGTH: 63
<212> TYPE: DNA
<213> ORGANISM: cytomegalovirus

<400> SEQUENCE: 12
taaaagagcc cacaacccct cactcggcgc gccagtcctc cgatagactg cgtcgcccgg   60
ggc                                                                63

<210> SEQ ID NO 13
<211> LENGTH: 64
<212> TYPE: DNA
<213> ORGANISM: cytomegalovirus

<400> SEQUENCE: 13
ctactgtgag ccccttacct gtagctgaga tccacgagcc gctagccccg ggcgacgcag   60
tcta                                                               64

<210> SEQ ID NO 14
<211> LENGTH: 64
<212> TYPE: DNA
<213> ORGANISM: cytomegalovirus

<400> SEQUENCE: 14
ttctcctgtt ccaactgttc ttggccctga gcggggcagg aactgcttac cacagatatc   60
ctgt                                                               64

<210> SEQ ID NO 15
<211> LENGTH: 1380
<212> TYPE: DNA
<213> ORGANISM: Homo sapien
<220> FEATURE:
<221> NAME/KEY: CDS
<222> LOCATION: (1)...(1380)

<400> SEQUENCE: 15 atg gat gca atg aag aga ggg ctc tgc tgt gtg ctg ctg ctg tgt ggc    48
Met Asp Ala Met Lys Arg Gly Leu Cys Cys Val Leu Leu Leu Cys Gly
 1               5                  10                  15 gcc gtc ttc gtt tcg ctc agc cag gaa atc cat gcc gag ttg aga cgc    96
Ala Val Phe Val Ser Leu Ser Gln Glu Ile His Ala Glu Leu Arg Arg
             20                  25                  30 ttc cgt aga tct gaa ggc tcc agt gtg aat ctg tca cct cca ctc gag   144
Phe Arg Arg Ser Glu Gly Ser Ser Val Asn Leu Ser Pro Pro Leu Glu
         35                  40                  45 cag tgt gtc cct gat cgg ggg cag cag tac cag ggg cgc ctg gcg gtg   192
Gln Cys Val Pro Asp Arg Gly Gln Gln Tyr Gln Gly Arg Leu Ala Val
     50                  55                  60 acc aca cat ggg ctc ccc tgc ctg gcc tgg gcc agc gca cag gcc aag   240
Thr Thr His Gly Leu Pro Cys Leu Ala Trp Ala Ser Ala Gln Ala Lys
 65                  70                  75                  80 gcc ctg agc aag cac cag gac ttc aac tca gct gtg cag ctg gtg gag   288
Ala Leu Ser Lys His Gln Asp Phe Asn Ser Ala Val Gln Leu Val Glu
                 85                  90                  95 aac ttc tgc cgc aac cca gac ggg gat gag gag ggc gtg tgg tgc tat   336
Asn Phe Cys Arg Asn Pro Asp Gly Asp Glu Glu Gly Val Trp Cys Tyr
            100                 105                 110
```

```
gtg gcc ggg aag cct ggc gac ttt ggg tac tgc gac ctc aac tat tgt     384
Val Ala Gly Lys Pro Gly Asp Phe Gly Tyr Cys Asp Leu Asn Tyr Cys
            115                 120                 125 gag gag gcc gtg gag gag gag aca gga gat ggg ctg gat gag gac tca     432
Glu Glu Ala Val Glu Glu Glu Thr Gly Asp Gly Leu Asp Glu Asp Ser
130                 135                 140 gac agg gcc atc gaa ggg cgt acc gcc aca agt gag tac cag act ttc     480
Asp Arg Ala Ile Glu Gly Arg Thr Ala Thr Ser Glu Tyr Gln Thr Phe
145                 150                 155                 160 ttc aat ccg agg acc ttt ggc tcg gga gag gca gac tgt ggg ctg cga     528
Phe Asn Pro Arg Thr Phe Gly Ser Gly Glu Ala Asp Cys Gly Leu Arg
                165                 170                 175 cct ctg ttc gag aag aag tcg ctg gag gac aaa acc gaa aga gag ctc     576
Pro Leu Phe Glu Lys Lys Ser Leu Glu Asp Lys Thr Glu Arg Glu Leu
            180                 185                 190 ctg gaa tcc tac atc gac ggg cgc att gtg gag ggc tcg gat gca gag     624
Leu Glu Ser Tyr Ile Asp Gly Arg Ile Val Glu Gly Ser Asp Ala Glu
        195                 200                 205 atc ggc atg tca cct tgg cag gtg atg ctt ttc cgg aag agt ccc cag     672
Ile Gly Met Ser Pro Trp Gln Val Met Leu Phe Arg Lys Ser Pro Gln
210                 215                 220 gag ctg ctg tgt ggg gcc agc ctc atc agt gac cgc tgg gtc ctc acc     720
Glu Leu Leu Cys Gly Ala Ser Leu Ile Ser Asp Arg Trp Val Leu Thr
225                 230                 235                 240 gcc gcc cac tgc ctc ctg tac ccg ccc tgg gac aag aac ttc acc gag     768
Ala Ala His Cys Leu Leu Tyr Pro Pro Trp Asp Lys Asn Phe Thr Glu
                245                 250                 255 aat gac ctt ctg gtg cgc att ggc aag cac tcc cgc acc agg tac gag     816
Asn Asp Leu Leu Val Arg Ile Gly Lys His Ser Arg Thr Arg Tyr Glu
            260                 265                 270 cga aac att gaa aag ata tcc atg ttg gaa aag atc tac atc cac ccc     864
Arg Asn Ile Glu Lys Ile Ser Met Leu Glu Lys Ile Tyr Ile His Pro
        275                 280                 285 agg tac aac tgg cgg gag aac ctg gac cgg gac att gcc ctg atg aag     912
Arg Tyr Asn Trp Arg Glu Asn Leu Asp Arg Asp Ile Ala Leu Met Lys
290                 295                 300 ctg aag aag cct gtt gcc ttc agt gac tac att cac cct gtg tgt ctg     960
Leu Lys Lys Pro Val Ala Phe Ser Asp Tyr Ile His Pro Val Cys Leu
305                 310                 315                 320 ccc gac agg gag acg gca gcc agc ttg ctc cag gct gga tac aag ggg    1008
Pro Asp Arg Glu Thr Ala Ala Ser Leu Leu Gln Ala Gly Tyr Lys Gly
                325                 330                 335 cgg gtg aca ggc tgg ggc aac ctg aag gag acg tgg aca gcc aac gtt    1056
Arg Val Thr Gly Trp Gly Asn Leu Lys Glu Thr Trp Thr Ala Asn Val
            340                 345                 350 ggt aag ggg cag ccc agt gtc ctg cag gtg gtg aac ctg ccc att gtg    1104
Gly Lys Gly Gln Pro Ser Val Leu Gln Val Val Asn Leu Pro Ile Val
        355                 360                 365 gag cgg ccg gtc tgc aag gac tcc acc cgg atc cgc atc act gac aac    1152
Glu Arg Pro Val Cys Lys Asp Ser Thr Arg Ile Arg Ile Thr Asp Asn
370                 375                 380 atg ttc tgt gct ggt tac aag cct gat gaa ggg aaa cga ggg gat gcc    1200
Met Phe Cys Ala Gly Tyr Lys Pro Asp Glu Gly Lys Arg Gly Asp Ala
385                 390                 395                 400 tgt gaa ggt gac agt ggg gga ccc ttt gtc atg aag agc ccc ttt aac    1248
Cys Glu Gly Asp Ser Gly Gly Pro Phe Val Met Lys Ser Pro Phe Asn
                405                 410                 415 aac cgc tgg tat caa atg ggc atc gtc tca tgg ggt gaa ggc tgt gac    1296
Asn Arg Trp Tyr Gln Met Gly Ile Val Ser Trp Gly Glu Gly Cys Asp
```

```
                  420              425              430
cgg gat ggg aaa tat ggc ttc tac aca cat gtg ttc cgc ctg aag aag      1344
Arg Asp Gly Lys Tyr Gly Phe Tyr Thr His Val Phe Arg Leu Lys Lys
        435              440              445 tgg ata cag aag gtc att gat cag ttt gga gag taa                      1380
Trp Ile Gln Lys Val Ile Asp Gln Phe Gly Glu  *
    450              455

<210> SEQ ID NO 16
<211> LENGTH: 2769
<212> TYPE: DNA
<213> ORGANISM: Homo sapien
<220> FEATURE:
<221> NAME/KEY: CDS
<222> LOCATION: (171)...(1016)

<400> SEQUENCE: 16
gaattcgaat tcctttgttt ccactgggac ggaatcggag ctctggaggc tgggctggcc      60 aagcgcccg aaggcccgat gcctgacggc tcatgcggcc tccttgtttg cagggcctgg     120
gcaaaaattt acactgagtc ccactcttcg ctccagggcc cggcaggaag atg ggc       176
                                                       Met Gly
                                                         1 tcc cgt gga cag gga ctc ttg ctg gcg tac tgc ctg ctc ctt gcc ttt      224
Ser Arg Gly Gln Gly Leu Leu Leu Ala Tyr Cys Leu Leu Leu Ala Phe
        5                  10                  15 gcc tct ggc ctg gtc ctg agt cgc gtg ccc cat gtc cag ggg gaa cag      272
Ala Ser Gly Leu Val Leu Ser Arg Val Pro His Val Gln Gly Glu Gln
    20                  25                  30 cag gag tgg gag ggg act gag gag ctg ccg tcc cct ccg gac cat gcc      320
Gln Glu Trp Glu Gly Thr Glu Glu Leu Pro Ser Pro Pro Asp His Ala
35                  40                  45                  50 gag agg gct gaa gaa caa cat gaa aaa tac agg ccc agt cag gac cag      368
Glu Arg Ala Glu Glu Gln His Glu Lys Tyr Arg Pro Ser Gln Asp Gln
                55                  60                  65 ggg ctc cct gct tcc cgg tgc ttg cgc tgc tgt gac cct ggt acc tcc      416
Gly Leu Pro Ala Ser Arg Cys Leu Arg Cys Cys Asp Pro Gly Thr Ser
            70                  75                  80 atg tac ccg gcg acc gcc gtg ccc cag atc aac atc act atc ttg aaa      464
Met Tyr Pro Ala Thr Ala Val Pro Gln Ile Asn Ile Thr Ile Leu Lys
        85                  90                  95 ggg gag aag ggt gac cgc gga gat cga ggc ctc caa ggg aaa tat ggc      512
Gly Glu Lys Gly Asp Arg Gly Asp Arg Gly Leu Gln Gly Lys Tyr Gly
    100                 105                 110 aaa aca ggc tca gca ggg gcc agg ggc cac act gga ccc aaa ggg cag      560
Lys Thr Gly Ser Ala Gly Ala Arg Gly His Thr Gly Pro Lys Gly Gln
115                 120                 125                 130 aag ggc tcc atg ggg gcc cct ggg gag cgg tgc aag agc cac tac gcc      608
Lys Gly Ser Met Gly Ala Pro Gly Glu Arg Cys Lys Ser His Tyr Ala
                135                 140                 145 gcc ttt tcg gtg ggc cgg aag aag ccc atg cac agc aac cac tac tac      656
Ala Phe Ser Val Gly Arg Lys Lys Pro Met His Ser Asn His Tyr Tyr
            150                 155                 160 cag acg gtg atc ttc gac acg gag ttc gtg aac ctc tac gac cac ttc      704
Gln Thr Val Ile Phe Asp Thr Glu Phe Val Asn Leu Tyr Asp His Phe
        165                 170                 175 aac atg ttc acc ggc aag ttc tac tgc tac gtg ccc ggc ctc tac ttc      752
Asn Met Phe Thr Gly Lys Phe Tyr Cys Tyr Val Pro Gly Leu Tyr Phe
    180                 185                 190 ttc agc ctc aac gtg cac acc tgg aac cag aag gag acc tac ctg cac      800
Phe Ser Leu Asn Val His Thr Trp Asn Gln Lys Glu Thr Tyr Leu His
```

-continued

```
          195                 200                 205                 210
atc atg aag aac gag gag gag gtg gtg atc ttg ttc gcg cag gtg ggc      848
Ile Met Lys Asn Glu Glu Glu Val Val Ile Leu Phe Ala Gln Val Gly
                    215                 220                 225 gac cgc agc atc atg caa agc cag agc ctg atg ctg gag ctg cga gag      896
Asp Arg Ser Ile Met Gln Ser Gln Ser Leu Met Leu Glu Leu Arg Glu
                230                 235                 240 cag gac cag gtg tgg gta cgc ctc tac aag ggc gaa cgt gag aac gcc      944
Gln Asp Gln Val Trp Val Arg Leu Tyr Lys Gly Glu Arg Glu Asn Ala
            245                 250                 255 atc ttc agc gag gag ctg gac acc tac atc acc ttc agt ggc tac ctg      992
Ile Phe Ser Glu Glu Leu Asp Thr Tyr Ile Thr Phe Ser Gly Tyr Leu
        260                 265                 270 gtc aag cac gcc acc gag ccc tag ctggccggcc acctcctttc ctctcgccac    1046
Val Lys His Ala Thr Glu Pro  *
275                 280 cttccacccc tgcgctgtgc tgacccagg gctcagcacc aggctgaccc caccgcctct    1106
tccccgatcc ctggactccg actccctggc tttggcattc agtgagacgc cctgcacaca    1166
cagaaagcca aagcgatcgg tgctcccaga tcccgcagcc tctggagaga gctgacggca    1226
gatgaaatca ccaggcgggg gcaccgcgca gaaccctctg ggaccttccg cggccctctc    1286
tgcacacatc ctcaagtgac cccgcacggc gagacgcggg tggcggcagg gcgtcccagg    1346
gtgcggcacc gcggctccag tccttggaaa taattaggca aattctaaag gtctcaaaag    1406
gagcaaagta aaccgtggag gacaaagaaa agggttgtta tttttgtctt ccagccagc    1466 ctgctggctc caagagaga ggccttttca gttgagactc tgcttaagag aagatccaaa    1526
gttaaagctc tggggtcagg ggaggggccg ggggcaggaa actacctctg cttaattct    1586 tttaagccac gtaggaactt tcttgaggga taggtggacc ctgacatccc tgtggccttg    1646
cccaagggct ctgctggtct ttctgagtca cagctgcgag gtgatggggg ctggggcccc    1706
aggcgtcagc ctcccagagg gacagctgag ccccctgcct tggctccagg ttggtagaag    1766
cagccgaagg gctcctgaca gtggccaggg accctgggt ccccaggcc tgcagatgtt     1826 tctatgaggg gcagagctcc tggtacatcc atgtgtggct ctgctccacc cctgtgccac    1886
cccagagccc tgggggtgg tctccatgcc tgccaccctg gcatcggctt tctgtgccgc     1946
ctcccacaca aatcagcccc agaaggcccc ggggctttgg cttctgtttt ttataaaaca    2006
cctcaagcag cactgcagtc tcccatctcc tcgtgggcta agcataccg cttccacgtg     2066 tgttgtgttg gttggcagca aggctgatcc agacccttc tgcccccact gccctcatcc     2126
aggcctctga ccagtagcct gagaggggct ttttctaggc ttcagagcag gggagagctg    2186 gaagggcta gaaagctccc gcttgtctgt ttctcaggct cctgtgagcc tcagtcctga    2246
gaccagagtc aagaggaagt acacatccca atcacccgtg tcaggattca ctctcaggag    2306
ctgggtggca ggagaggcaa tagcccctgt ggcaattgca ggaccagctg gagcagggtt    2366
gcggtgtctc cgcggtgctc tcgccctgcc catggccacc ccagactctg atctccagga    2426
accccatagc ccctctccac ctcacccat gttgatgccc aggtcactc ttgctacccg     2486 ctgggccccc aaaccccgc tgcctctctt ccttcccccc atccccacc tggttttgac     2546 taatcctgct tccctctctg ggcctggctg ccgggatctg gggtccctaa gtccctctct    2606
```

```
ttaaagaact tctgcgggtc agactctgaa gccgagttgc tgtgggcgtg cccggaagca    2666
gagcgccaca ctcgctgctt aagctccccc agctctttcc agaaaacatt aaactcagaa    2726
ttgtgttttc agcaaaaaaa aaaaaaaaaa aaagggcggc cgc                      2769
```